United States Patent [19]

Pineyro-Lopez

[11] Patent Number: 5,578,646

[45] Date of Patent: Nov. 26, 1996

[54] PHARMACEUTICALLY ACCEPTABLE ANTHRACENE COMPOUNDS

[75] Inventor: Alfredo Pineyro-Lopez, Rio Mississippi #253 Ote., Col. Del Valle, Nuevo Leon, Mexico

[73] Assignee: Alfredo Pineyro-Lopez, Mexico

[21] Appl. No.: 733,191

[22] Filed: Jul. 19, 1991

[30] Foreign Application Priority Data

Jul. 20, 1990 [DE] Germany ................. 40 23 159.3

[51] Int. Cl.$^6$ ................................................. A61K 31/12
[52] U.S. Cl. ................................................. 514/680
[58] Field of Search ................................. 514/680

[56] References Cited

U.S. PATENT DOCUMENTS 4,283,390  8/1981  Koch et al. ........................ 424/122
4,670,265  6/1987  Sydiskis et al. ................... 424/195.1

FOREIGN PATENT DOCUMENTS 2044231   7/1977  Japan ............................. A01N 9/24
62/207213  9/1987  Japan.

OTHER PUBLICATIONS

Chemical Abstracts, vol. 107, 1987, Abstract No. 230651; Guerrero et al.; Toxicon; vol. 25, No. 5, pp. 565–568; 1987.
Chemical Abstracts, vol. 110, 1989, Abstract No. 228622e; Kitanaka et al.; Chem. Pharm. Bull., vol. 37, No. 2, 1989; pp. 511–512.
Chemical Abstracts, vol. 80, 1974; Abstract No. 12461r; Steglich et al.; Zeitung Naturforschung, Teil C, vol. 28, No. 5–6, 1973, pp. 255–259.
Chemical Abstracts, vol. 80, 1974; Abstract No. 12463t; Steglich et al.; Zeitung Naturforshcung, Teil C, vol. 28, No. 5–6, 1973, pp. 354–355.
Chemical Abstracts, vol. 78, 1973; Abstract No. 4001j; Steglich et al.; Phytochemistry, vol. 11, No. 11, 1972, pp. 3299–3304.
"Hagers Handbuch der Pharmazeutischen Praxis," Vierte Neuausgabe, V. Band Chemikalien und Drogen (H–M).
D. L. Dreyer, I. Aral, C. D. Bachman, W. R. Anderson, Jr., R. G. Smith and G. D. Daves, Jr., "Toxins Causing Noninflammatory Paralytic Neuronopathy. Isolation and Structure Elucidation," *J. Am. Chem. Soc.*, 97:17 (Aug. 20, 1975).
M. Guerrero, A. Pineyro and N. Waksman, "Extraction and Quantification of Toxins from *Karwinskia humboldtiana* (Tullidora), *Toxicon*", vol. 25, No. 5, pp. 565–568 (1987).
M. V. Bermudez, D. Gonzalez–Spencer, M. Guerrero, N. Waksman and A. Pineyro, "Experimental Intoxication with Fruit and Purified Toxins of Buckthorn (*Karwinskia humboldtiana*), Toxicon", vol. 24, Nos. 11–12, pp. 1091–1097 (1986).
N. Waksman, L. Martinez, "Chemical and Toxicological Screening in Genus Karwinskia (Mexico)," *Rev. Latinoamer. Quim.*, vol. 20, No. 1, pp. 27–29 (1989).
International Congress on Natural Products Research, American Society of Pharmacognosy & Japanese Society of Pharmacognosy, 29th Annual Meeting of the American Society of Pharmacology (Jul. 17–21, 1988).
S. Kitanaka and M. Takido, "Studies on the Constituents of the Roots of *Cassia torosa*. II. The Structures of Two Dimeric Tetrahydroanthracenes," *Chem. Pharm. Bull.*, vol. 38, No. 5, pp. 1292–94 (1990).
Omura et al 90 CA:119686b 1979.
Kakinuma et al 93CA:233347d 1980.
Roth et al 114CA:17555e 1990—Jun. 13 1990.
Konoshima et al 113CA:204402u 1989.
Kitanaka et al 113CA:108782x 1990.
Toshio et al 112CA:84202j 1989.
Takito et al 110CA:82476m 1987.
Dagne et al 109CA:22736R 1987.
Avery's Dry Treatment, 3rd Edition 1988, pp. 1039–1055.

*Primary Examiner*—Russell Travers
*Attorney, Agent, or Firm*—Bacon & Thomas

[57] ABSTRACT

The invention concerns the use of bis-anthracene compounds isolated from *Karwinskia humboldtiana* in therapy. The compounds of the invention are selective with a high margin of safety relative to malignant tumor cells and therefore are suitable in particular in the treatment of liver, lung and colon carcinomas and further in the treatment of viral diseases.

1 Claim, No Drawings

PHARMACEUTICALLY ACCEPTABLE ANTHRACENE COMPOUNDS

The invention concerns specific anthracene compounds for therapeutic applications, and also pharmaceuticals containing these compounds.

*Karwinskia humboldtiana* is a bush of the rhamnaceae family which is common in the semi-deserts of North and Central America and in the southwestern U.S.A. and is described for instance in Hagers Handbuch Der Pharmazeutischen Praxis, 4th ed., 5th vol., p 397. This plant drew attention because paralysis symptoms have been observed upon ingestion of or tasting plant parts, similar to those of the Guillain-Barre syndrome, of poliomyelitis and other peripheral polyneuropathies. Further, extraneuronal damage was reported in sheep and goats.

Most research has been directed to the fruit. Dreyer et al in *J. Am. Chem. Soc.* 1975, 97, 4986 were able to isolate and fractionate four dimeric anthracene compounds from the endocarp of such fruit. These compounds were defined in relation to their molecular weights by T-496, T-514, T-516 and T-544.

Now it has been surprisingly discovered that the compounds of the invention evince a selective cytostatic and a cytotoxic and antiviral effect. The effect on tumor cells is especially advantageous.

Accordingly, the present invention concerns the compounds of formula 1,

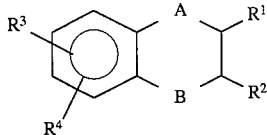

where A is C=O or C—OH,

B is CH—$R^5$ or C—$R^5$, the ring comprising the A and B groups being aromatic if A is C—OH and B is C—$R^5$, $R^1$ and $R^2$ may be the same or different and represent a $C_1$–$C_4$ acyl group, $C_1$–$C_4$ alkyl group, $C_1$–$C_4$ alkoxy group or $R^1$ and $R^2$ together with the carbon atoms to which they are bound represent a phenyl, a cyclohexanon or a tetrahydropyran ring which may be substituted by at least one residue selected from among a $C_1$–$C_4$ alkoxy group, a hydroxy group, and a $C_1$–$C_4$ acyloxy group, $R^3$ is a $C_1$–$C_4$ alkyl group, $C_1$–$C_4$ alkoxy group, $C_1$–$C_4$ acyloxy group or hydroxy group, and one of the residues $R^4$ and $R^5$ is a hydrogen atom and the other is a group of formula

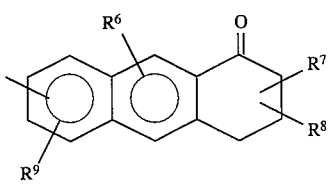

wherein $R^6$, $R^7$, $R^8$ and $R^9$ represent a $C_1$–$C_4$ alkyl group, a $C_1$–$C_4$ alkoxy group, a $C_1$–$C_4$ alkoxy group or a hydroxy group, and their tautomeric forms, position isomers and optical isomers.

A preferred embodiment is represented by the compounds of formula,

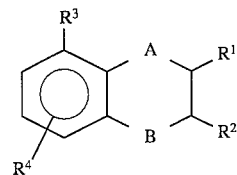

where A, B and $R^1$–$R^4$ are defined as above.

Preferably the residue $R^4$ is bound in the ortho position to the residue $R^3$ on the phenyl ring.

Further preferred embodiments are the compounds of formulas 1.1, 1.2 and 1.3:

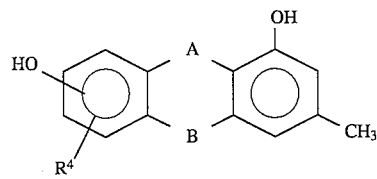

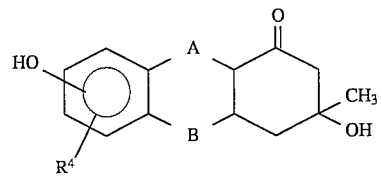

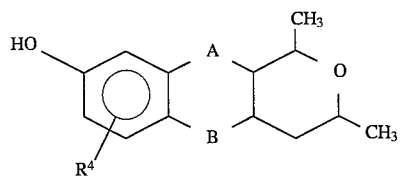

The compounds of formula 1 with $R^1$ representing a $C_1$–$C_4$ alkyl group, in particular an acetyl group, and $R^2$ a $C_1$–$C_4$ alkyl group, in particular a methyl group, are another preferred embodiment.

In the above formulas, one of the residues $R^4$ and $R^5$ and in particular the residue $R^5$ represents a group of the formula

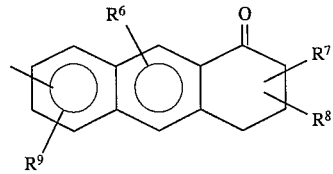

Preferably $R^6$, $R^9$ and one of the residues $R^7$ and $R^8$ represent a hydroxy group and the other of the residues $R^7$ and $R^8$ represents a $C_1$–$C_4$ alkyl group, in particular a methyl group.

In an especially preferred embodiment, one of the residues $R^4$ and $R^5$ represents a group of formula

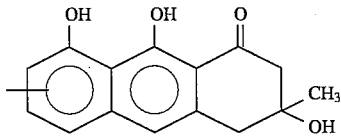

which is bound in particular by its 2-position to the skeleton.

Preferably the residue $R^3$ in the above formulas represents a hydroxy group.

The following are especially preferred compounds:

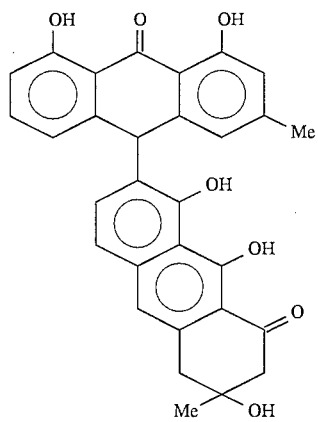
(T-496) (I)
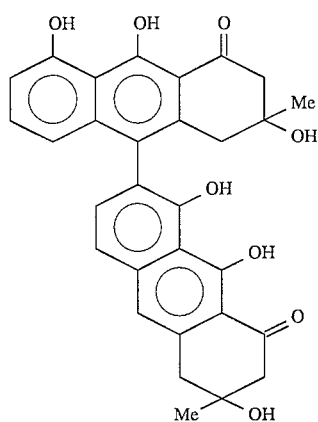
(T-514) (II)
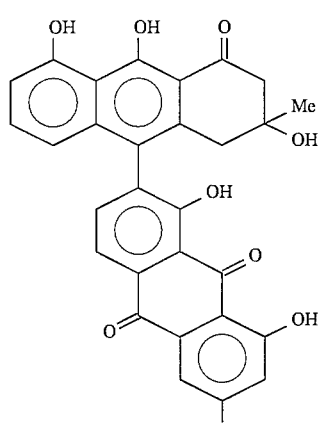
(T-510) (III)

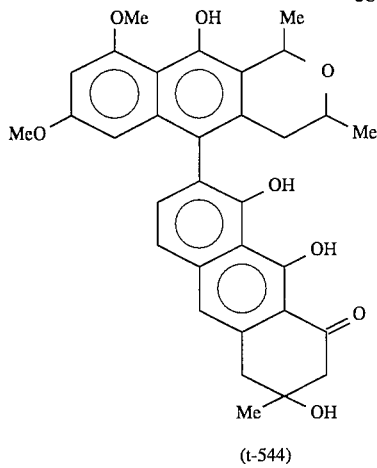

(t-544)

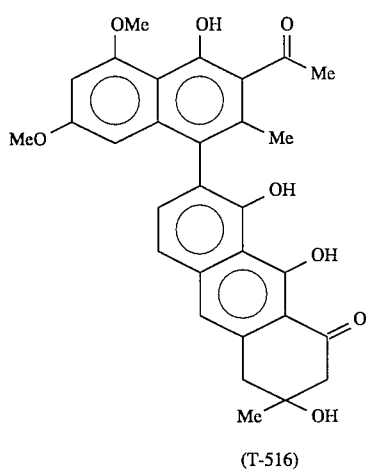

(T-516)

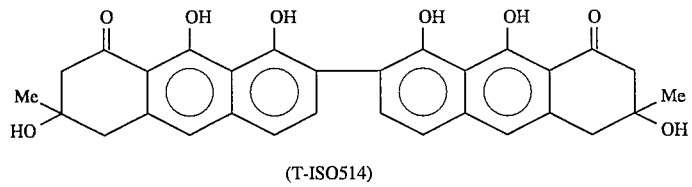

(T-ISO514)

These compounds are identified by the stated abbreviation referring to the molecular weight.

The process for preparing the compounds of the invention consists in isolating them from the fruit of the Karwinskia species (or from other plants containing the compounds of the invention). For that purpose, the fruit are conventionally dried and comminuted. Then a non-polar, organic solvent such as pentane, hexane, petroleum ether, etc. is used for defatting. The defatted fruit are then extracted with a solvent of average polarity. Suitable solvents are chlorinated aliphatic hydrocarbons such as chloroform, methylene chloride, ethylene dichloride, etc. The extraction is performed conventionally, using from 3 to 10-fold the amount of solvent in relation to the fruit to be extracted (V/G). Appropriately, the extract is concentrated prior to further processing, for instance to one-tenth to one-twentieth of the initial volume. Where called for the solvent also may be entirely removed and the residue may be reprocessed as described below.

Adding a non-polar organic solvent such as pentane, hexane, petroleum ether, etc. to the concentrated extract, a product is then precipitated which contains one (or several of the) compound(s) of the invention. This product is isolated conventionally for instance by thin-film or column chromatography or by fractionated crystallization.

The compounds so obtained can be conventionally converted, for instance by esterification, etherification, ester and ether hydrolysis, substitution reactions at the aromatic nucleus, oxidations and reductions, into other compounds of the invention.

Illustratively the compounds T514, 496, 544 and 516 can be isolated from the fruit of Karwinskia humboldtiana by the method described in J. Am. Chem. Soc. 97, 4986 (1975). Another method to isolate T-514 is described in Toxicon, 25, No. 5, 565–568 (1987).

Pharmacological research has shown that the cytostatic and cytotoxic effects of the compounds of the invention are very selective, in particular relative to liver, lung and colon tissue. The compounds of the invention can distinguish between benign and malignant types of cells. Therefore, they are suitable to treat liver, lung and colon carcinomas. It was found moreover that the compounds of the invention evince anti-viral properties and therefore are suitable in the treatment of viral disease, for instance herpes simplex I, II and III.

The compounds of the invention may be administered either singly as therapeutic active substances or together with other therapeutic active substances. While they may be administered as such, as a rule they will be administered in the form of pharmaceutical agents, that is as a mixture of the active substances with suitable pharmaceutical excipients and/or inactive substances. The compounds or agents can be administered orally or parenterally, preferably the latter. For that purpose the active substances are used with conventional excipients, for instance in the form of infusion solutions.

The preparation of the pharmaceutical agents takes place conventionally by integrating the active substance into a pharmaceutical excipient and/or inactive ingredient.

In therapy, the compounds of the invention can be administered to mammals (humans and animals) in doses of about 0.01 to about 2 mg, preferably about 0.01 to about 1 mg and especially about 0.01 to about 0.5 mg, or about 0.01 to about 0.1 mg, per kg of body weight a day. They may be administered in a single dose or in several divided ones. The stated dose range is only illustrative. The physician obviously shall determine the most suitable dose, with such factors as age, weight, the disease being treated, the gravity and site of the disease being taken into account.

The Examples below elucidate the invention.

EXAMPLE 1

Preparation of 3,3',8,8',9,9'-hexahydroxy-3,3,4,4-tetrahydro-(7,10')-bisanthracene-1,1'-(2H-2H')-dione (T-514) of formula

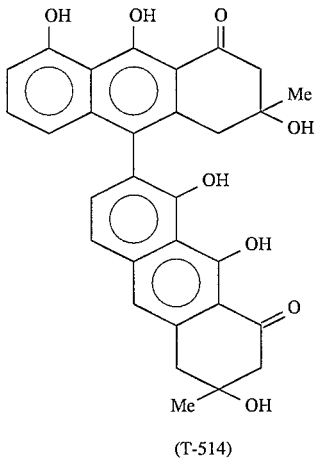

(T-514)

500 g of dried and comminuted fruit of *Karwinskia humboldtiana* are extracted consecutively with 3 liters of petroleum ether (boiling-point range about 60° to 70° C.) and 3 liters of chloroform. The chloroform extract is concentrated to 100 ml and the product is precipitated by twice adding 300 ml of n-hexane. The yellow powder so obtained is fractionated on silica gel G (layer thickness 0.5 mm) using benzene:acetone (2:1) as the mobile solvent. The fraction with the lowest $R_f$ value is the T-514 compound. This fraction is scratched off the chromatographic plate and is back eluted with acetone. The product is further purified on acetylated polyamide (layer thickness 0.5 mm) with methanol:$H_2O$ (2:1) as the mobile solvent. Following recrystallization from benzene-hexane, pure T-514 is obtained (50 mg). Melting point: 130° C. $^1$H-NMR and $^{13}$C-NMR spectra are listed in Table 1, Example 2. $LD_{50}$ (following intraperitoneal administration to mouse): 6.52±0.86 mg/kg.

EXAMPLE 2

Preparation of T-514' (optical isomer of T-514)

500 g dried and ground fruit of Karwinskia parvifolia were extracted consecutively with 3 liters each of petroleum ether, chloroform and methanol. Each extraction took place over 3 days at room temperature. Following evaporation of the solvent, the chloroform extract was separated on silica gel using benzene:acetone (3:1), 0.1% acetic acid, into three fractions. Each fraction was purified further by chromatography on silica gel and acetylated polyamide. Compounds denoted by T-496 and T-514 were isolated respectively from the 1st and 3rd fractions and the desired T-514' compound from the 2nd fraction. Recrystallization of T-514' from benzene-hexane results in a yellow powder (450 mg) with a melting point of 169° to 171° C.

UV (MeOH)$_{max}$ 220 (4.83), 266 (4.97), 408 (4.38);

IR: 3360, 1625, 1350, 1250; EIMS: m/z (rel. intens.) $M^+$514 (30), 478 (80), 240 (10), 43 (100)

The NMR spectra of T-514 and T-514' are listed in Tables 1 and 2 below.

TABLE 1

$^1$H NMR of T-514 and T-514'
(Solvent: DMSO; J in parentheses is in Hz).

| H | T514 | T514' | H | T514 | T514' |
|---|------|-------|---|------|-------|
| 2 | 2.87 | 3.00 | 2' | 2.85 | 2.95 |
| 3-Me | 1.45 | 1.3 | 3'-Me | 1.31 | 1.15 |
| 4 | 3.13 | 3.1 (17.5) | 4' | 2.91 (16.7) | 2.90 (17.5) |
|   |      | 3.0 (17.5) |    | 2.70 (16.7) | 2.70 (17.5) |
| 5 | 7.35 (8.0) | 7.39 (8.0) | 5' | 6.7 (8.3) | 6.6 (8,25) |
| 6 | 7.32 (8.0) | 7.34 (8.1) | 6' | 7.33 (8.3 and 7.8) | 7.34 (8.25 and 7.65) |
| 10 | 7.1 | 7.2 | 7' | 6.83 (7.8) | 6.8 (7.65) |
| 8 OH | 9.98 | 9.95 | 8'OH | 9.90 | 9.70 |
| 9 OH | 16.00 | 15.99 | 9'OH | 16.38 | 16.15 |

TABLE 2

$^{13}$C NMR of T 514 and T 514'
(Solvent: DMSO; a,b,c,d,e,f,g,h,i,j: at those positions, the arrangement also may be reversed)

| C | T 514 |   | T 514' |   | C | T 514 |   | T 514' |   |
|---|-------|---|--------|---|---|-------|---|--------|---|
| 1 | 203.2 | a | 205.28 | f | 1' | 203.7 | a | 205.53 | f |
| 2 | 50.84 |   | 50.83  |   | 2' | 51.16 |   | 51.02 |   |
| 3 | 71.02 | b | 69.68  | g | 3' | 70.08 | b | 69.21 | g |
| 4 | 43.14 |   | 42.41  |   | 4' | 40.99 |   | 40.64 |   |
| 4a | 135.13 |   | 138.60 |   | 4'a | 135.13 |   | 138.60 |   |
| 5 | 118.59 |   | 118.79 |   | 5' | 117.01 |   | 116.50 |   |
| 6 | 135.16 |   | 135.09 |   | 6' | 132.63 |   | 132.14 |   |
| 7 | 119.93 |   | 119.40 |   | 7' | 111.159 |   | 110.45 |   |
| 8 | 115.38 |   | 154.47 |   | 8' | 158.51 |   | 157.62 |   |
| 8a | 112.98 | c | 112.10 | h | 8'a | 112.81 | c | 112.02 | h |
| 9 | 165.61 |   | 163.98 |   | 9' | 165.49 |   | 163.63 |   |
| 9a | 109.22 | d | 109.46 | i | 9'a | 109.74 | d | 109.98 | i |
| 10 | 118.50 |   | 117.87 |   | 10' | 125.26 |   | 124.61 |   |

TABLE 2-continued

13C NMR of T 514 and T 514'
(Solvent: DMSO; a,b,c,d,e,f,g,h,i,j: at those positions,
the arrangement also may be reversed)

| C | T 514 | T 514' | | C | T 514 | T 514' | |
|---|-------|--------|---|---|-------|--------|---|
| 10a | 139.34 | 137.18 | | 10'a | 139.34 | 137.18 | |
| CH₃ | 29.12 | e | 28.93 | j | CH₃' | 29.22 | e | 29.02 | j |

EXAMPLE 3

Isolating T-510 of formula:

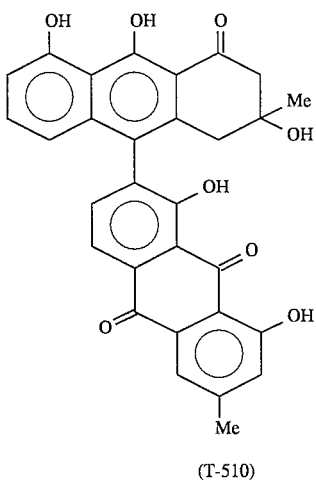

(T-510)

500 g dried, comminuted fruit of *Karwinskia affin humboldtiana* are consecutively extracted with 3 liters of petroleum ether (boiling-point range: 60°–70° C.) and 3 liters of chloroform. The chloroform extract is concentrated to 100 ml and the product is precipitated by adding 300 ml n-hexane. The powder so prepared is purified by layer chromatography on silica gel with benzene:acetone (3:1) as the solvent. The fraction of highest $R_f$ is purified on a silica gel tower with benzene:acetone (40:1) as the mobile solvent. The fraction so prepared is exposed to light for 24 h, filtered and then purified by chromatography on acetylated polyamide using CHCl₃/MeOH (30:1) and precipitated with a mixture of benzene:acetone. The yield is 60 mg. Melting point: 136°14 138° C.

UV: $\lambda_{max}$ 423 (4.28), 314 (4.78), 264 (4.70), 226 (4.78)
IR (cm⁻¹): 3400, 1720, 1690, 1630, 1270, 750

| ¹H-NMR | | | |
|---|---|---|---|
| H | δ | H | δ |
| 2 | 7.14 | 2' | 2.88 |
| 3-Me | 2.5 | 3'-CH₃ | 1.4 |
| 4 | 7.67 | 4' | 2.7 (J = 16 Hz) |
| | | | 2.9 (J = 16 Hz) |
| 5 | 8.06(J = 7.6) | 5' | 6.68 (J = 8, 2 Hz) |
| 6 | 7.66(J = 7.6) | 6' | 7.4 (J = 8, 3 Hz) |
| | | 7' | 6.88 (J = 8.3 Hz) |
| 8-OH | 12.02 | 8'-OH | 10.1 |
| 1-OH | 12.37 | 9'-OH | 16.04 |

EXAMPLE 4

Isolating T-496 of formula

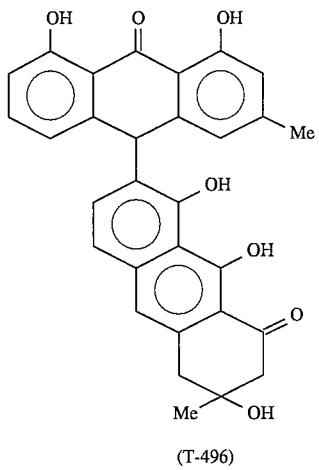

(T-496)

500 g dried, comminuted fruit of *Karwinskia humboldtiana* are consecutively extracted with 3 liters of petroleum ether (boiling-point range about 60°–70° C.) and 3 liters of chloroform. The chloroform extract is concentrated to 100 ml and the product is precipitated by twice adding 300 ml n-hexane. The resultant yellow powder is fractionated on silica gel G (layer thickness 0.5 mm) using benzene:acetone (2:1) as the mobile solvent. The fraction of highest $R_f$ value is chromatographed on a silica-gel column using benzene::acetone (40:1) as the solvent. The pure product is precipitated using benzene:hexane. Yield: 50 mg pure powder. Melting point: 230° C.

UV: $\lambda_{max}$ 227 (4.66), 273 (4.71), 397 (4.15)
IR (cm⁻¹): 3415, 1635, 1620, 1600

| ¹H-NMR | | | |
|---|---|---|---|
| H | δ | H | δ |
| 2 | 2.00 | 1'-OH | 12.20 |
| 3-Me | 1.40 | 2' | 6.60 |
| 4 | 3.05 | 3'-Me | 2.20 |
| 5 | 7.15 | 4' | 6.60 |
| 6 | 7.15 | 5' | 6.75 |
| | | 6' | 7.3 |
| 8-OH | 10.00 | 7' | 6.8 |
| 9-OH | 16.00 | | |
| 10 | 6.90 | 8'-OH | 12.30 |
| | | 10' | 6.10 |

EXAMPLE 5

Isolating T ISO 514 of formula

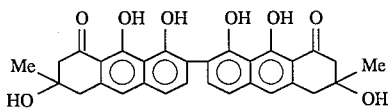

500 g dried, comminuted fruit of *Karwinskia umbelleta* are consecutively extracted with 3 liters of petroleum ether (boiling point 60°–70° C.) and 3 liters of chloroform. The chloroform extract is concentrated to 100 ml and the product is precipitated by addition of 300 ml n-hexane. The resulting powder is purified by layer chromatography on silica gel using benzene:acetone (2:1) as the solvent. the fraction of lowest $R_f$ is subjected to column chromatography with silica gel. The product is eluted with benzene:acetone (1:1) and then is purified in a Sephadex column LH with MeOH as solvent. Precipitation with n-hexane provides 30 mg of pure product. Melting point: 161°–164° C.

UV: $\lambda_{max}$ 422 (3.75), 270 (4.64), 220 (4.1)

IR (cm$^{-1}$): 3400, 1 630, 1600

| H | $^1$H-NMR δ |
|---|---|
| H-2 | 2.7 (J = 16) |
|  | 3.0 (J = 16) |
| 3-CH3 | 2.4 |
| H-4 | 3.5 (J = 16) |
|  | 3.10 (J = 16) |
| H-5 | 7.58 (J = 8.4) |
| H-6 | 7.3 (J = 8.4) |
| H-10 | 7.14 |
| 8-OH | 9.9 |
| 9-OH | 16.05 |

EXAMPLE 6

Isolating T-544 of formula

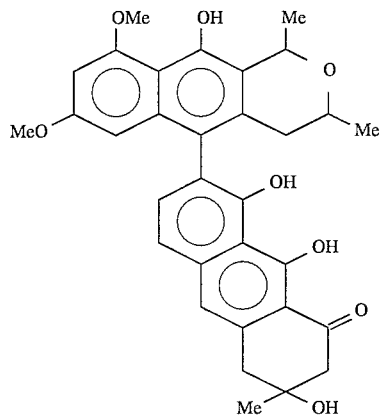

500 g dried, comminuted fruit of *Karwinskia humboldtiana* are consecutively extracted with 3 liters of petroleum ether (boiling-point range about 60°–70° C.) and 3 liters of chloroform. The chloroform extract is concentrated to 100 ml and the product is precipitated by twice adding 300 ml of n-hexane. The resulting yellow powder is fractionated on silica gel G (layer thickness 0.5 mm) using benzene:acetone (2:1) as mobile solvent. The fraction with the average $R_f$ value is purified by column chromatography on silica gel and with benzene:acetone (20:1) as the mobile solvent. After new chromatography and precipitation with n-hexane, 200 mg of pure product are obtained. Melting point: 166°–168° C.

UV(MeOH) $\lambda_{max}$ 228 (4.67), 242 (4.77), 270 (4.63), 415 (4.00)

IR (cm$^{-1}$): 3390, 1625

| H | $^1$H-NMR H |  |  |
|---|---|---|---|
|  |  | 1' | 5.26 |
| 2 | 2.85 | 1$^+$-Me | 1.69 |
| 3 Me | 1.46 | 3' | 3.7 |
|  |  | 3'-Me | 1.21 |
| 4 | 3.1 | 4' | 2.35 |

| H | $^1$H-NMR H |  |  |
|---|---|---|---|
| 5 | 7.26 | 6' | 6.27 |
| 6 | 7.41 | 7'-O Me | 3.56 |
| 10 | 7.00 | 8' | 6.41 |
|  |  | 9'-O Me | 4.00 |
| 8-OH | 9.8 |  |  |
| 9-OH | 16.00 | 10' | 9.6 |

EXAMPLE 7

Cytoxicity of T-514

Cells of human origin are used for this test. Benign Chang liver cells are used as hepatic cells and three cell lines are used as neoplastic cells, i.e. Hepatom PLC/PRF/5, Hep3B with the surface antigen of hepatitis B and Hep2B without antigen.

Benign pulmonary epithelial cells Wi 1003 were used as the cells of pulmonary origin and the neoplastic cells were four cell lines, namely squamous carcinoma SK-mes-1, adenocarcinoma Calu, undifferentiated bronchogenic carcinoma Cha-Go-K-1 and microcytic carcinoma NCl-H 69.

Benign colon epithelial cells CCD-33Co are used as colon cells and the neoplastic cells are the colonadenocarcinoma cell line LoVo.

A mixture of Eagle's basal medium and sheep fetus serum (9+1) was used as the cell culture medium for all investigated cell lines. The test substances were dissolved in ethanol or water and were added to the cell cultures in the concentrations (µg/ml)listed below:

| T-514 | 2.5, 5, 10, 20, 40, 80, 160, 320 |
|---|---|
| Doxorubicin | 0.025, 0.05, 0.1, 0.2, 0.4, 0.8, 1.6, 3.2, 6.4 |
| 4 Epidoxorubicin | 0.025, 0.05, 0.1, 0.2, 0.4, 0.8, 1.6, 3.2, 6.4 |
| Vincristin | 0.002, 0.004, 0.008, 0.0156, 0.03125, 0.0625, 0.125, 0.25, 0.05, 1, 2, 4, 8, 16 |
| 5-Fluoruracil | 6.25, 12.5, 25, 50, 100, 200, 400, 800, 1600, 3200 |
| Mitomycin | 0.25, 0.5, 1, 2, 3, 4, 8, 16 |

In the control tests, the solvent was used without the test substances.

Following incubation for 72 h, analysis was carried out in a conventional manner of determining desmosome adhesion, morphology and cell proliferation.

The test results are shown in the form of the modified therapeutic index $LD_{05}\%/ED_{95}\%$.

The values were extrapolated from the corresponding curves. The modified therapeutic index lists the selectivity of the test substances, that is, a positive therapeutic index shows that the neoplastic cells react more sensitively to the test substances than do benign ones, whereas the reverse is the case for a negative modified therapeutic index. Table 3 shows the results.

TABLE 3

| | Modified therapeutic index | | | | | $LD_{05\%}$/$ED_{95\%}$ |
|---|---|---|---|---|---|---|
| | DOXO | EPI | MITO | VINC | FLUO | T-514 |
| H$_2$ | −1.877 | −1.119 | −1.869 | −13.636 | −2.588 | 14.257 |
| H$_3$ | −14.973 | −7.459 | −1.555 | −2035.818 | −2.214 | 8.565 |
| H$_4$ | −14.973 | −8.963 | −1.555 | −435.100 | −3.110 | 8.565 |
| IND. | 1.073 | 2.146 | −1.867 | −15.189 | −1.107 | 4.282 |
| ADE. | −1.867 | −1.071 | −1.555 | −15.189 | −1.107 | 4.282 |

TABLE 3-continued

| | | | | | | |
|---|---|---|---|---|---|---|
| SCH. | −3.730 | −1.865 | −1.867 | −30.189 | −2.588 | 2.573 |
| KDE. | −3.106 | −1.553 | −1.555 | −15.189 | −6.620 | 8.565 |
| K.K | −2.589 | −3.313 | 2.573 | −7.426 | 5.060 | 17.129 |

| | CODES | |
|---|---|---|
| $H_2$ hepatoma cell | PLC/PRF/5 | |
| $H_3$ liver cell carcinoma | HEP 3B | |
| $H_4$ liver cell carcinoma | HEP G2 | |
| IND bronchial carcinoma | CHa Go K-1 | |
| ADE pulmonary adenocarcinoma | Calu + 3 | |
| SCH pulmonary squamous cell carcinoma | SK-Mes-1 | |
| KLE pulmonary microcytic carcinoma | NCI-B69 | |
| KK colon adenocarcinoma | LoVo | |
| DOXO doxorubicin | VINC | VINCRISTIN |
| MITO mitomycin | FLUO | 5-FLUORURACIL |

The result show that the T-514 compound is highly selective, that is, it evinces higher activity toward malignant than toward benign tumor cells. The compounds of the invention therefore are useful cytostatic and tumor drugs with a large safety margin.

I claim:
1. A method of treating a malignant tumor in a human which comprises administering a compound having the formula:

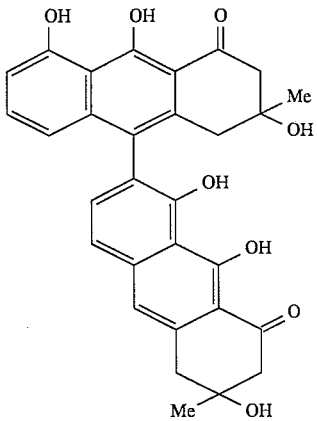

to said malignant tumor, wherein said tumor is a liver, lung or colon tumor.

* * * * *